United States Patent
Saijo et al.

(10) Patent No.: US 6,673,922 B2
(45) Date of Patent: Jan. 6, 2004

(54) PROCESS FOR PREPARING TRIAZINE COMPOUND AND QUATERNARY AMMONIUM SALTS

(75) Inventors: Masako Saijo, Tokuyama (JP); Naoki Hirano, Tokuyama (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 10/070,592

(22) PCT Filed: Jun. 29, 2001

(86) PCT No.: PCT/JP01/05650
§ 371 (c)(1),
(2), (4) Date: Mar. 8, 2002

(87) PCT Pub. No.: WO02/04430
PCT Pub. Date: Jan. 17, 2002

(65) Prior Publication Data
US 2002/0123628 A1 Sep. 5, 2002

(30) Foreign Application Priority Data
Jul. 10, 2000 (JP) ......................................... 2000-207802

(51) Int. Cl.$^7$ ...................... C07D 251/26; C07D 251/46
(52) U.S. Cl. ....................................... 544/113; 544/218
(58) Field of Search .................................. 544/113, 218

(56) References Cited

FOREIGN PATENT DOCUMENTS

GB    1 520 682    *  8/1978

OTHER PUBLICATIONS

Cronin et al. Synthetic Communications. 26(8) 3491–3494, 1996.*
Kunishima et al. Tetrahedron 55 13159–13170, 1999.*
Cronin, Jason S. et al., "An Improved Procedure for the Large Scale Preparation of 2–Chloro–4,6–Dimethoxy–1,3,5–Triazine", *Synthetic Communications*, 26(18), pp. 3491–3494, 1966 by Marcel Dekker, Inc.

* cited by examiner

Primary Examiner—Richard L. Raymond
Assistant Examiner—Venkataraman Balasubramanian
(74) Attorney, Agent, or Firm—Webb Ziesenheim Logsdon Orkin & Hanson, P.C.

(57) ABSTRACT

A high yield process for preparing 4,6-dialkoxy-1,3,5-triazine-2-halide by reacting a cyanuric halide with an alcohol compound such as methanol in the presence of an alkali such as sodium hydrogencarbonate, wherein the water content present in the reaction system at the beginning of the reaction is controlled to not more than 0.5 mol based on 1 mol of the cyanuric halide or the water content present in the reaction system during the period of the reaction is controlled to not more than 2.5 mol based on 1 mol of the cyanuric halide.

6 Claims, No Drawings

PROCESS FOR PREPARING TRIAZINE COMPOUND AND QUATERNARY AMMONIUM SALTS

TECHNICAL FIELD

The present invention relates to a process for preparing a triazine compound in a high yield, said triazine compound being useful as an intermediate of pharmaceuticals or agricultural chemicals, and a process for preparing a quaternary ammonium salt using the triazine compound obtained by the above process, said quaternary ammonium salt being useful as a condensation agent.

BACKGROUND ART

A quaternary ammonium salt wherein a nitrogen atom at the 4-position of morpholine such as 4-(4,6-dimethoxy-1,3,5-triazin-2-yl)-4-methylmorpholinium chloride is quaternized and to the nitrogen atom are bonded a 4,6-dialkoxy-1,3,5-triazin-2-yl group and an alkyl group is a useful compound as a condensation agent for preparing an ester compound or an amide compound.

The quaternary ammonium salt can be prepared by reacting 2-halo-4,6-dialkoxy-1,3,5-triazine with 4-alkylmorpholine, and as a process for preparing the triazine compound, there is known a process comprising allowing an alcohol compound to act on cyanuric chloride in the presence of 3 mol of sodium hydrogencarbonate and 2.7 mol of water based on 1 mol of the cyanuric chloride (SYNTHETIC COMMUNICATIONS, Vol. 26, No. 18, pp. 3491–3494, 1996).

In the above process, however, the yield of the triazine compound is as low as 65% and is not satisfactory. The present invention overcomes this shortcoming by providing a process for preparing the triazine compound in a high yield and, in addition, provides a process for efficiently preparing the quaternary ammonium salt.

SUMMARY OF THE INVENTION

The present invention recognizes that the yield of the triazine compound is remarkably increased when the water content present in the reaction system at the beginning of the reaction or the water content present in the reaction system during the period of the reaction is greatly decreased by the use of a hydrogencarbonate in the form of an organic solvent suspension or the like. This is in contrast to the conventional process wherein an alcohol compound is reacted with cyanuric chloride, wherein the hydrogencarbonate is used in the form of an aqueous solution and, hence, a large amount of water is present in the reaction system. The present invention recognizes that when the water content at the beginning of the reaction is controlled to not more than a specific value, the desired product can be obtained in a high yield even if water formed by the reaction as a by-product is not removed.

Briefly stated, the present invention is a process for preparing a triazine compound (2-halo-4,6-dialkoxy-1,3,5-triazine) represented by the following formula (I):

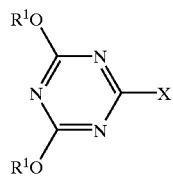

wherein
  $R^1$ is an alkyl group of 1 to 4 carbon atoms or an aryl group of 6 to 8 carbon atoms, and X is a halogen atom,
  said process comprising reacting a cyanuric halide with an alcohol compound represented by the following formula:

$R^1OH$ wherein
  $R^1$ is an alkyl group of 1 to 4 carbon atoms or an aryl group of 6 to 8 carbon atoms,
  in the presence of an alkali to prepare the triazine compound represented by the above formula (I),
  wherein the water content present in the reaction system at the beginning of the reaction is not more than 0.5 mol based on 1 mol of cyanuric halide.

Another embodiment of the present invention is a process for preparing the triazine compound, comprising reacting a cyanuric halide with the alcohol compound in the presence of an alkali to prepare the triazine compound, wherein the water content present in the reaction system during the period of the reaction is not more than 2.5 mol based on 1 mol of cyanuric halide.

In the present invention, a hydrogencarbonate is particularly preferably used as the alkali.

According to the process of the invention for preparing a triazine compound, the desired product can be obtained in a high yield.

The present invention further provides a process for preparing a quaternary ammonium salt represented by the following formula (III):

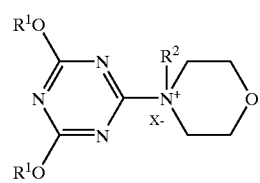

wherein
  $R^1$ is an alkyl group of 1 to 4 carbon atoms or an aryl group of 6 to 8 carbon atoms, $R^2$ is an alkyl group of 1 to 4 carbon atoms, and X is a halogen atom,
  said process comprising extracting a triazine compound represented by the above formula (I) from the reaction solution containing the triazine compound using a slightly water-soluble organic solvent and then mixing the resulting slightly water-soluble organic solution of the triazine compound with a morpholine compound represented by the following formula (II) to perform reaction;

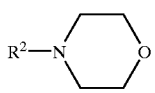

(II)

wherein $R^2$ is an alkyl group of 1 to 4 carbon atoms.

According to the above process, production efficiency of the triazine compound is high, and hence, from the viewpoint of the total production process starting from the primary materials such as an alcohol compound and a cyanuric halide, the quaternary ammonium salt that is the final desired product can be prepared efficiently.

DETAILED DESCRIPTION OF THE INVENTION

The process for preparing a triazine compound according to the invention is not particularly different from the conventional process comprising reacting a cyanuric halide with an alcohol compound in the presence of an alkali, except that the amount of water present in the reaction system at the beginning of the reaction is controlled to not more than a specific value or the amount of water present in the reaction system during the period of the reaction is controlled to not more than a specific value.

That is to say, as the cyanuric halide, conventionally known compounds are employable without any restriction, and examples thereof include cyanuric chloride, cyanuric bromide and cyanuric iodide. Of these, cyanuric chloride that is particularly easily obtainable can be preferably employed.

As the alcohol compound, an alcohol compound represented by the following formula is employable.

wherein $R^1$ is an alkyl group of 1 to 4 carbon atoms or an aryl group of 6 to 8 carbon atoms.

Examples of the alcohol compounds employable in the invention include methanol, ethanol, propanol, isopropyl alcohol, butanol, tert-butyl alcohol, phenol, cresol and xylenol. Of these, an alkyl alcohol compound of 1 to 4 carbon atoms, such as methanol, ethanol, propanol, isopropyl alcohol or butanol, is preferably used from the viewpoint of usefulness of the quaternary ammonium salt (final desired product) as the condensation agent.

In the present invention, the alcohol compound has only to be used in an amount of 2 mol or more based on 1 mol of the cyanuric halide from the viewpoint of the stoichiometry. From the viewpoint of high reaction efficiency, however, it is preferable that the alcohol compound also have a function of a reaction solvent. When using the alcohol compound as the reaction solvent, too small amount of the alcohol causes aggregation or solidification to bring about troubles in stirring or the like, and hence, it is preferable to use the alcohol compound in an amount of 5 to 50 mol, particularly 5 to 30 mol, based on 1 mol of the cyanuric halide.

The alkali employable in the invention is, for example, a basic salt such as a hydrogencarbonate, an organic amine or an inorganic amine, and a hydrogencarbonate is particularly preferably employed. As the hydrogencarbonate, conventionally known compounds are employed without any restriction. Examples of the hydrogencarbonates employable in the invention include sodium hydrogencarbonate, potassium hydrogencarbonate and ammonium hydrogencarbonate. Of these, sodium hydrogencarbonate and potassium hydrogencarbonate are preferably employed.

If the amount of the alkali is too small, hydrogen chloride formed by the reaction of the alcohol compound with the cyanuric halide is not neutralized, and thereby the progress of the reaction becomes difficult. If the amount thereof is too large, the slurry viscosity becomes high to cause troubles in stirring or the like. Hence, the amount of the alkali is desirably selected from the range of 2 to 3 mol, preferably 2.05 to 2.8 mol, based on 1 mol of the cyanuric halide.

In the process for preparing a triazine compound according to the invention, an inert organic solvent is also employable in addition to the alcohol compound. Examples of the organic solvents employable in the invention include aromatic hydrocarbons, such as benzene, toluene and xylene; aliphatic hydrocarbons, such as hexane and heptane; halogenated aliphatic hydrocarbons, such as dichloromethane and carbon tetrachloride; esters, such as ethyl acetate, propyl acetate and butyl acetate; ethers, such as diethyl ether, diisopropyl ether, 1,4-dioxane and tetrahydrofuran; nitrites, such as acetonitrile and propionitrile; amides, such as N,N-dimethylformamide, N,N-dimethylacetamide and N-methylpyrrolidone; and dimethylsulfoxide. These organic solvents may be used singly or in combination of two or more kinds. The amount of the organic solvent used is not specifically limited, but from the viewpoint of the reaction rate, the amount thereof is preferably not more than 100 times by mol, more preferably not more than 10 times by mol. particularly preferably not more than once by mol, to the number of moles of the alcohol compound.

In the process for preparing a triazine compound according to the invention, the water content present in the reaction system at the beginning of the reaction needs to be controlled to not more than 0.5 mol based on 1 mol of the cyanuric halide or the water content present in the reaction system during the period of the reaction needs to be controlled to not more than 2.5 mol based on 1 mol of the cyanuric halide, in order to obtain the desired triazine compound in a high yield. If the water content at the beginning of the reaction exceeds 0.5 mol based on 1 mol of the cyanuric halide or if the water content during the period of the reaction exceeds 2.5 mol based on 1 mol of the cyanuric halide, the triazine compound cannot be obtained in a high yield. From the viewpoint of high yield of the desired product, the water content present in the reaction system at the beginning of the reaction is controlled to preferably not more than 0.2 mol, more preferably not more than 0.1 mol, particularly preferably not more than 0.05 mol, based on 1 mol of the cyanuric halide, or the water content present in the reaction system during the period of the reaction is controlled to preferably not more than 2.2 mol, more preferably not more than 2.1 mol, particularly preferably not more than 2.05 mol, based on 1 mol of the cyanuric halide.

There is no specific limitation on the method to decrease the water content at the beginning of the reaction or during the period of the reaction. For example, it is quite enough to use the alkali in the form of not an aqueous solution but an organic solvent suspension and to use each of the reaction agents and the reaction solvent after sufficient drying. The water content in each reaction agent can be measured by Karl Fischer's method, gas chromatography, thermobalance method, or the like.

With progress of the reaction of the alcohol with the cyanuric halide, water is formed by the reaction as a by-product in an amount of 2 mol based on 1 mol of the cyanuric halide, but by controlling the water content at the beginning of the reaction to not more than 0.5 mol based on 1 mol of the cyanuric halide, the desired product can be obtained in a high yield even if any dehydration operation is not carried out during the course of the reaction. In order to obtain the desired product in a higher yield, however, it is preferable to prevent inclusion of water from the outside during the reaction and thereby control the water content present in the system during the reaction by, for example, conducting the reaction in a dry gas atmosphere.

The method to react the cyanuric halide with the alcohol compound in the presence of the alkali is not specifically limited, except that the water content in the reaction system at the beginning of the reaction is controlled to not more than 0.5 mol based on 1 mol of the cyanuric halide. However, hydrogen chloride is formed by the reaction, so that it is preferable to add the alkali (particularly hydrogencarbonate) to the alcohol and then add the cyanuric halide to contact the cyanuric halide with the alcohol and thereby perform reaction.

The concentration of the cyanuric halide is not specifically limited, but if the concentration is too low, the yield per batch is lowered, which is economically disadvantageous. If the concentration is too high, troubles are encountered in stirring or the like. Hence, the concentration of the cyanuric halide is desirably selected from the range of 0.1 to 60% by weight, preferably 1 to 50% by weight.

There is no specific limitation on the reaction temperature, but if the temperature is too low, the reaction rate is decreased, and if the temperature is too high, the side reaction is promoted. Hence, the reaction temperature is desirably selected from the range of the usual solidification point of the system to the boiling point of the system, preferably 0 to 100° C. The reaction time greatly varies depending upon the type of the alcohol or the type of the hydrogencarbonate and cannot be derided indiscriminately. A reaction time of 1 to 24 hours is satisfactory. The reaction can be practiced under any of reduced pressure, atmospheric pressure and pressurizing.

By performing the reaction under the above reaction conditions, the triazine compound represented by the formula (I), i.e., 2-halo-4,6-dialkoxy-1,3,5-triazine, is efficiently produced.

The triazine compound can be isolated by extracting the triazine compound with a slightly water-soluble organic solvent and then distilling off the organic solvent.

The triazine compound thus obtained can be used as it is in the subsequent reaction. According to necessity, however, it may be purified prior to use. For the purification, conventionally known methods are employable without any restriction. For example, the purification can be made by recrystallization.

The triazine compound produced can be isolated by such an isolation operation as described above, but for example, it is possible to prepare a quaternary ammonium salt represented by the following formula (III):

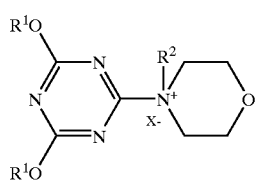

(III)

wherein
$R^1$ is an alkyl group of 1 to 4 carbon atoms or an aryl group of 6 to 8 carbon atoms, $R^2$ is an alkyl group of 1 to 4 carbon atoms, and X is a halogen atom,
by extracting the triazine compound from the reaction solution containing the triazine compound using a slightly water-soluble organic solvent and then mixing the resulting slightly water-soluble organic solution of the triazine compound with a morpholine compound represented by the following formula (II) to perform reaction;

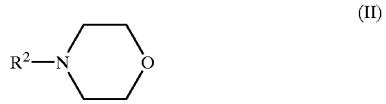

(II)

wherein $R^2$ is an alkyl group of 1 to 4 carbon atoms.

Examples of the morpholine compounds represented by the formula (II) include 4-methylmorpholine, 4-ethylmorpholine and 4-isobutylmorpholine. These morpholine compounds are all readily available as reagents and industrial materials.

In the synthesis of the quaternary ammonium salt, the amount of the morpholine compound represented by the formula (II) used is not specifically limited, but it is preferable to use this compound in an amount of 0.7 to 1.3 mol, particularly 0.8 to 1.2 mol, based on 1 mol of the triazine compound represented by the formula (I).

For extracting the triazine compound, excess alcohol is distilled off from the reaction solution to the utmost, then water is added to completely dissolve the salt, and from the resulting aqueous solution, the triazine compound is extracted with a slightly water-soluble organic solvent. As the slightly water-soluble organic solvent for the extraction, organic solvents which separate from an aqueous layer and do not inhibit the reaction of the triazine compound with the morpholine compound can be used without any restriction. Examples of the organic solvents employable herein include ethers, such as tetrahydrofuran, 1,4-dioxane, diethyl ether and diisopropyl ether; halogenated aliphatic hydrocarbons, such as methylene chloride, chloroform and carbon tetrachloride; esters, such as ethyl acetate and propyl acetate; ketones, such as methyl isobutyl ketone; aromatic hydrocarbons, such as benzene, toluene and xylene; halogenated aromatic hydrocarbons, such as chlorobenzene and dichlorobenzene; aliphatic hydrocarbons, such as hexane and heptane; and carbonates, such as dimethyl carbonate. Of these, organic solvents which can be expected to give a high isolation yield, i.e., ethers, such as tetrahydrofuran, 1,4-dioxane, diethyl ether and diisopropyl ether; halogenated aliphatic hydrocarbons, such as methylene chloride and chloroform; esters, such as ethyl acetate and propyl acetate; ketones, such as methyl isobutyl ketone; aromatic hydrocarbons, such as benzene, toluene and xylene; and carbonates, such as dimethyl carbonate, are preferably adopted.

For the purpose of removing impurities, the organic solution of the extracted triazine compound may be washed with an acid aqueous solution and a basic aqueous solution. Examples of the acids preferably used include mineral acids, such as hydrochloric acid, sulfuric acid, nitric acid and phosphoric acid, and organic acids, such as acetic acid and citric acid. Examples of the bases preferably used include alkalimetal hydroxides, such as sodium hydroxide and potassium hydroxide, and alkali metal carbonates, such as sodium carbonate, potassium carbonate, sodium hydrogencarbonate and potassium hydrogencarbonate. Although the concentration of the acid aqueous solution and the basic aqueous solution is not specifically limited, an aqueous solution of usually 0.1 to 10% by weight is preferably adopted.

There is no specific limitation on the amount of the organic solvent used, but if the amount thereof is too large, the yield per batch is lowered to provide an economic disadvantage, and if the amount thereof is too small, troubles develop in stirring or the like. Hence, the amount of the organic solvent is desirably selected so that the concentration of the quaternary ammonium salt represented by the formula (III) is 0.1 to 60% by weight, preferably 1 to 50% by weight.

In order to easily obtain a high-purity quaternary ammonium salt for a short period of time, water or an alcohol may be allowed to be present in an amount of 0.1 to 10 mol, preferably 0.2 to 8 mol, based on 1 mol of the triazine compound, in the reaction of the triazine compound with the morpholine compound in the organic solvent. The alcohol used herein is preferably an alkyl alcohol of 1 to 4 carbon atoms.

The reaction of the triazine compound with the morpholine compound can be carried out by contacting these compounds in an organic solvent. For homogeneously carrying out the reaction for a short period of time, it is preferable to conduct stirring. The reaction is usually feasible in air, but when the compound used or the reaction product is hygroscopic, it is preferably to conduct the reaction in dry air, the air having been passed through a drying tube such as a calcium chloride tube or in an inert gas atmosphere such as nitrogen, helium or argon. The reaction may be carried out under any of reduced pressure, atmospheric pressure and pressurizing.

There is no specific limitation on the reaction temperature, but if the temperature is too low, the reaction rate is decreased, and if the temperature is too high, the side reaction is promoted. Hence, the reaction temperature is desirably selected from the range of usually −20 to 70° C., preferably −10 to 60° C. Although the reaction time is not specifically limited, a reaction time of usually 0.1 to 10 hours is quite enough.

The quaternary ammonium salt represented by the formula (III) produced as above is usually precipitated as crystals, so that the solid is separated by general solid-liquid separation, such as centrifugal separation, centrifugal filtration, pressure, filtration or vacuum filtration, and then dried by general drying, such as air drying or vacuum drying, to obtain the quaternary ammonium salt.

When crystals are not precipitated, the organic solvent used is removed to the utmost, then a solvent such as tetrahydrofuran is added to make a slurry, and the quaternary ammonium salt is obtained from the slurry in the same manner as described above.

The quaternary ammonium salt obtained as above can be used as a condensation agent which is used for, for example, preparing an amide compound by the reaction of a carboxylic acid compound with an amine compound or preparing an ester compound by the reaction of a carboxylic acid compound with an alcohol compound.

EXAMPLE

The present invention is further described with reference to the following examples, but the invention is in no way limited to those examples.

Example 1

In a 500-ml four-necked flask equipped with a stirrer and a thermometer, 44.1 g (0.525 mol) of sodium hydrogencarbonate and 160.2 g (water content: 650 ppm, 5.0 mol) of methanol were placed. With stirring at a temperature of not higher than 10° C., 46.1 g (0.25 mol) of cyanuric chloride was added, followed by stirring at 20° C. for 1 hour. Then, the reaction was conducted at 60° C. for 3.5 hours. The weight of the reaction solution from which a salt formed had been removed was 192 g, and the water content was 49,500 ppm. After cooling, methanol was distilled off. To the residue, 200 ml of water was added, and the objective product was extracted with 250 ml of ethyl acetate. The organic layer was washed with 100 ml of water and then vacuum concentrated to obtain 39.2 g of 2-chloro-4,6-dimethoxy-1,3,5-triazine as a white solid. The yield was 89.2%. From the gas chromatography analysis, the purity proved to be 96.3% (% by area).

The water content at the beginning of the reaction was 0.023 mol based on 1 mol of the cyanuric chloride, and the water content in the system during the reaction was 2.11 mol based on 1 mol of the cyanuric chloride.

Example 2

In a 500-ml four-necked flask equipped with a stirrer and a thermometer, 52.6 g (0.525 mol) of potassium hydrogencarbonate and 160.2 g (water content: 340 ppm, 5.0 mol) of methanol were placed. With stirring at a temperature of not higher than 10° C., 46.1 g (0.25 mol) of cyanuric chloride was added, followed by stirring at 20° C. for 1 hour. Then, the reaction was conducted at 50° C. for 2.5 hours. The weight of the reaction solution from which a salt formed had been removed was 193 g, and the water content was 49,600 ppm. After cooling, methanol was distilled off. To the residue, 200 ml of water was added, and the objective product was extracted with 250 ml of ethyl acetate. The organic layer was washed with 100 ml of water and then vacuum concentrated to obtain 38.8 g of 2-chloro-4,6-dimethoxy-1,3,5-triazine as a white solid. The yield was 88.3%. From the gas chromatography analysis, the purity proved to be 96.0% (% by area).

The water content at the beginning of the reaction was 0.012 mol based on 1 mol of the cyanuric chloride, and the water content in the system during the reaction was 2.12 mol based on 1 mol of the cyanuric chloride.

Example 3

In a 1-liter (1000-ml) four-necked flask equipped with a stirrer and a thermometer, 88.2 g (1.05 mol) of sodium hydrogencarbonate and 160.2 g (water content: 460 ppm, 5.0 mol) of methanol were placed. With stirring at a temperature of not higher than 10° C., 92.2 g (0.5 mol) of cyanuric chloride was added, followed by stirring at 20° C. for 1 hour. Then, the reaction was conducted at 60° C. for 3.5 hours. The weight of the reaction solution from which a salt formed had been removed was 233 g, and the water content was 80,300 ppm. After cooling, methanol was distilled off. To the residue, 400 ml of water was added, and the objective product was extracted with 500 ml of ethyl acetate. The organic layer was washed with 400 ml of water and then vacuum concentrated to obtain 74.4 g of 2-chloro-4,6-dimethoxy-1,3,5-triazine as a white solid. The yield was 84.8%. From the gas chromatography analysis, the purity proved to be 97.4% (% by area).

The water content at the beginning of the reaction was 0.008 mol based on 1 mol of the cyanuric chloride, and the water content in the system during the reaction was 2.08 mol based on 1 mol of the cyanuric chloride.

Example 4

In a 1-liter (1000-ml) four-necked flask equipped with a stirrer and a thermometer, 105.1 g (1.05 mol) of potassium hydrogencarbonate and 160.2 g (5.0 mol, water content: 530 ppm) of methanol were placed. With stirring at a temperature of not higher than 10° C., 92.2 g (0.5 mol) of cyanuric chloride was added, followed by stirring at 20° C. for 1 hour. Then, the reaction was conducted at 50° C. for 4 hours. The weight of the reaction solution from which a salt formed had been removed was 230 g, and the water content was 79,800 ppm. After *cooling, methanol was distilled off. To the residue, 400 ml of water was added, and the objective product was extracted with 500 ml of ethyl acetate. The organic layer was washed with 400 ml of water and then vacuum concentrated to obtain 72.7 g of 2-chloro-4,6-dimethoxy-1,3,5-triazine as a white solid. The yield was 82.8%. From the gas chromatography analysis, the purity proved to be 94.9% (% by area).

The water content at the beginning of the reaction was 0.009 mol based on 1 mol of the cyanuric chloride, and the water content in the system during the reaction was 2.04 mol based on 1 mol of the cyanuric chloride.

Example 5

In a 1-liter (1000-ml) four-necked flask equipped with a stirrer and a thermometer, 44.1 g (0.525 mol) of sodium hydrogencarbonate, 80.1 g (2.5 mol, water content: 560 ppm) of methanol and 100 ml of ethyl acetate were placed. With stirring at a temperature of not higher than 10° C., 46.1 g (0.25 mol) of cyanuric chloride was added, followed by stirring at 20° C. for 1 hour. Then, the reaction solution was refluxed at 62° C. for 10 hours. The weight of the reaction solution from which a salt formed had been removed was 205 g, and the water content was 46,000 ppm. Then, 150 ml of ethyl acetate and 200 ml of water were added, followed by liquid separation. The organic layer was washed with 200 ml of water and then vacuum concentrated to obtain 37.0 g of 2-chloro-4,6-dimethoxy-1,3,5-triazine as a white solid. The yield was 84.3%. From the gas chromatography analysis, the purity proved to be 96.1% (% by area).

The water content at the beginning of the reaction was 0.010 mol based on 1 mol of the cyanuric chloride, and the water content in the system during the reaction was 2.10 mol based on 1 mol of the cyanuric chloride.

Example 6

In a 1-liter (1000-ml) four-necked flask equipped with a stirrer and a thermometer, 52.6 g (0.525 mol) of potassium hydrogencarbonate, 80.1 g (5.0 mol, water content: 530 ppm) of methanol and 100 ml of ethyl acetate were placed. With stirring at a temperature of not higher than 10° C., 46.1 g (0.25 mol) of cyanuric chloride was added, followed by stirring at 20° C. for 1 hour. Then, the reaction solution was refluxed at 62° C. for 6 hours. The weight of the reaction solution from which a salt formed had been removed was 202 g, and the water content was 46,300 ppm. Then, 150 ml of ethyl acetate and 200 ml of water were added, followed by liquid separation. The organic layer was washed with 200 ml of water and then vacuum concentrated to obtain 38.4 g of 2-chloro-4,6-dimethoxy-1,3,5-triazine as a white solid. The yield was 87.5%. From the gas chromatography analysis, the purity proved to be 93.8% (% by area).

The water content at the beginning of the reaction was 0.009 mol based on 1 mol of the cyanuric chloride, and the water content in the system during the reaction was 2.08 mol based on 1 mol of the cyanuric chloride.

Example 7

In a 1-liter (1000-ml) four-necked flask equipped with a stirrer and a thermometer, 92.4 g (1.1 mol) of sodium hydrogencarbonate and 391 g (8.5 mol, water content: 570 ppm) of ethanol were placed. With stirring at a temperature of not higher than 10° C., 92.2 g (0.5 mol) of cyanuric chloride was added, followed by stirring at 20° C. for 1 hour. Then, the reaction was conducted at 60° C. for 11 hours. The weight of the reaction solution from which a salt formed had been removed was 462 g, and the water content was 40,200 ppm. After cooling, ethanol was distilled off. To the residue, 200 ml of water was added, and the objective product was extracted with 250 ml of ethyl acetate. The organic layer was washed with 100 ml of water and then vacuum concentrated to obtain 87.9 g of 2-chloro-4,6-diethoxy-1,3,5-triazine as a white solid. The yield was 86.4%. From the gas chromatography analysis, the purity proved to be 94.8% (% by area).

The water content at the beginning of the reaction was 0.025 mol based on 1 mol of the cyanuric chloride, and the water content in the system during the reaction was 2.06 mol based on 1 mol of the cyanuric chloride.

Example 8

In a 500-ml four-necked flask equipped with a stirrer and a thermometer, 44.1 g (0.525 mol) of sodium hydrogencarbonate and 160.2 g (water content: 650 ppm, 5.0 mol) of methanol were placed. With stirring at a temperature of not higher than 10° C., 46.1 g (0.25 mol) of cyanuric chloride was added, followed by stirring at 20° C. for 1 hour. Then, the reaction was conducted at 60° C. for 3.5 hours. The weight of the reaction solution from which a salt formed had been removed was 192 g, and the water content was 49,000 ppm. The water content at the beginning of the reaction was 0.023 mol based on 1 mol of the cyanuric chloride, and the water content in the system during the reaction was 2.09 mol based on 1 mol of the cyanuric chloride.

After cooling, methanol was distilled off. To the residue, 200 ml of water was added, and 2-chloro-4,6-dimethoxy-1,3,5-triazine formed was extracted with 250 ml of ethyl acetate. Then, the organic layer was washed with 100 ml of water. The weight of the organic layer was 249.3 g, and the water content was 28,000 ppm. To the ethyl acetate solution of the 2-chloro-4,6-dimethoxy-1,3,5-triazine, 200 ml of ethyl acetate and 5.4 g of water were added, followed by stirring at 5 to 10° C. for 10 minutes. Then, 23.9 g (0.236 mol) of 4-methylmorpholine was added, and the reaction was conducted at 5 to 10° C. for 5 hours. The crystals precipitated were suction filtered, then washed with 100 ml of ethyl acetate and vacuum dried at room temperature for 6 hours to obtain 61.1 g of 4-(4,6-dimethoxy-1,3,5-triazin-2-yl)-4-methylmorpholinium chloride as a white solid. The water content in the white solid was 0.4% by weight, and the yield was 88.0%. From the high performance liquid chromatography analysis, the purity proved to be 99.3% (% by area).

Example 9

In a 500-ml four-necked flask equipped with a stirrer and a thermometer, 52.6 g (0.525 mol) of potassium hydrogencarbonate and 160.2 g (water content: 340 ppm, 5.0 mol) of methanol were placed. With stirring at a temperature of not higher than 10° C., 46.1 g (0.25 mol) of cyanuric chloride was added, followed by stirring at 20° C. for 1 hour. Then, the reaction was conducted at 50° C. for 2.5 hours. The weight of the reaction solution from which a salt formed had been removed was 193 g, and the water content was 49,100 ppm. The water content at the beginning of the reaction was 0.012 mol based on 1 mol of the cyanuric chloride, and the water content in the system during the reaction was 2.10 mol based on 1 mol of the cyanuric chloride.

After cooling, methanol was distilled off. To the residue, 200 ml of water was added, and 2-chloro-4,6-dimethoxy-1,3,5-triazine formed was extracted with 250 ml of ethyl acetate. Then, the organic layer was washed with 100 ml of water. The weight of the organic layer was 249.2 g, and the water content was 27,000 ppm. To the ethyl acetate solution of the 2-chloro-4,6-dimethoxy-1,3,5-triazine, 200 ml of ethyl acetate and 5.4 g of water were added, followed by stirring at 5 to 10° C. for 10 minutes. Then, 23.9 g (0.236 mol) of 4-methylmorpholine was added, and the reaction was conducted at 5 to 10° C. for 5 hours. Then, 8.1 g of water was added, followed by stirring for 10 minutes. The crystals precipitated were suction filtered, then washed with 100 ml of ethyl acetate and vacuum dried at room temperature for 3 hours to obtain 69.8 g of 4-(4,6-dimethoxy-1,3,5-triazin-2-yl)-4-methylmorpholinium chloride as a white solid. The water content in the white solid was 13.7% by weight, and the yield was 87.1%. From the high performance liquid chromatography analysis, the purity proved to be 99.5% (% by area).

Comparative Example 1

In a 500-ml four-necked flask equipped with a stirrer and a thermometer, 63.0 g (0.75 mol) of sodium hydrogencarbonate, 98.5 g (3.08 mol, water content: 187 ppm) of methanol and 12.1 g (0.675 mol) of water were placed. With stirring at a temperature of not higher than 10° C., 46.1 g (0.25 mol) of cyanuric chloride was added, followed by stirring for 30 minutes. Then, the reaction was conducted at 35° C. for 15 hours. The weight of the reaction solution from which a salt formed had been removed was 158 g, and the water content was 143,000 ppm. After cooling, methanol was distilled off. To the residue, 400 ml of water was added, and the objective product was extracted with 300 ml of ethyl acetate. The organic layer was washed with 100 ml of water and then vacuum concentrated to obtain 29.5 g of 2-chloro-4,6-dimethoxy-1,3,5-triazine. The yield was 67.2%. From the gas chromatography analysis, the purity proved to be 94.0% (% by area).

The water content at the beginning of the reaction was 2.70 mol based on 1 mol of the cyanuric chloride, and the water content in the system during the reaction was 5.02 mol based on 1 mol of the cyanuric chloride.

According to the process of the invention described above, a triazine compound is obtained from a cyanuric halide and an alcohol in a high yield, so as to demonstrate the industrial applicability of the present invention.

What is claimed is:

1. A process for preparing a triazine compound represented by the formula (I)

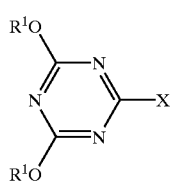

(I)

wherein
  $R^1$ is an alkyl group of 1 to 4 carbon atoms or an aryl group of 6 to 8 carbon atoms, and X is a halogen atom,
  said process comprising reacting a cyanuric halide with an alcohol compound represented by the following formula:

$R^1OH$ wherein
  $R^1$ is an alkyl group of 1 to 4 carbon atoms or an aryl group of 6 to 8 carbon atoms,
  in the presence of hydrogencarbonate to prepare the triazine compound represented by the above formula (I)
  wherein the water content present in the reaction system at the beginning of the reaction is not more than 0.5 mol based on 1 mol of cyanuric halide.

2. A process for preparing a triazine compound represented by the formula (I)

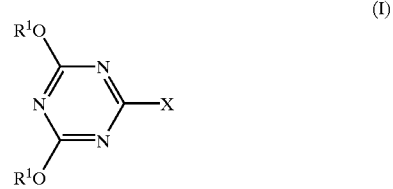

(I)

wherein
  $R^1$ is an alkyl group of 1 to 4 carbon atoms or an aryl group of 6 to 8 carbon atoms, and X is a halogen atom,
  said process comprising reacting a cyanuric halide with an alcohol compound represented by the following formula:

$R^1OH$ wherein
  $R^1$ is an alkyl group of 1 to 4 carbon atoms or an aryl group of 6 to 8 carbon atoms,
  in the presence of hydrogencarbonate to prepare the triazine compound represented by the above formula (I),
  wherein the water content present in the reaction system during the period of the reaction is not more than 2.5 mol based on 1 mol of cyanuric halide.

3. A process for preparing a quaternary ammonium salt represented by the following formula (III):

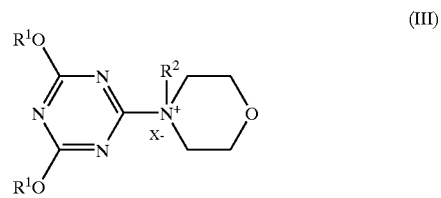

(III)

wherein
  $R^1$ is an alkyl group of 1 to 4 carbon atoms or an aryl group of 6 to 8 carbon atoms, X is a halogen atom,
  said process comprising extracting a triazine compound from the reaction solution containing the triazine compound obtained by the process of claim 1 using a slightly water-soluble organic solvent and then mixing the resulting slightly water-soluble organic solution of the triazine compound with a morpholine compound represented by the following formula (II) to perform reaction;

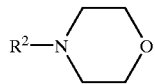
(II)

wherein $R^2$ is an alkyl group of 1 to 4 carbon atoms.

4. The process for preparing a triazine compound as claimed in claim 1, wherein the alcohol compound is employed in an amount of 5 to 50 mol based on 1 mol of cyanuric halide.

5. The process for preparing a triazine compound as claimed in claim 2, wherein the alcohol compound is employed in an amount of from 5 to 50 mol based on 1 mol of cyanuric halide.

6. A process for preparing a quaternary ammonium salt represented by the following formula (III):

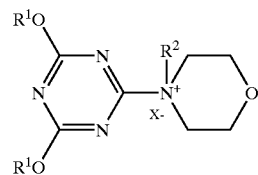
(III)

wherein
$R^1$ is an alkyl group of 1 to 4 carbon atoms or an aryl group of 6 to 8 carbon atoms, and X is a halogen atom, said process comprising extracting a triazine compound from the reaction solution containing the triazine compound obtained by the process of claim 2 using a slightly water-soluble organic solvent and then mixing the resulting slightly water-soluble organic solution of the triazine compound with a morpholine compound represented by the following formula (II) to perform reaction;

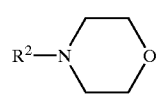
(II)

wherein $R^2$ is an alkyl group of 1 to 4 carbon atoms.

* * * * *

UNITED STATES PATENT AND TRADEMARK OFFICE
CERTIFICATE OF CORRECTION

PATENT NO.    : 6,673,922 B2
DATED         : January 6, 2004
INVENTOR(S)   : Masako Saijo et al.

It is certified that error appears in the above-identified patent and that said Letters Patent is hereby corrected as shown below:

Column 5,
Line 31, "cannot be derided" should read -- cannot be decided --.

Column 7,
Line 5 and 45, "quatemary" should read -- quaternary --.

Column 12,
Line 57, in the formula (III), "X-" should read -- X⁻ --.

Column 14,
Line 7, formula (III), "X-" should read -- X⁻ --.

Signed and Sealed this

Twenty-second Day of June, 2004

JON W. DUDAS
*Acting Director of the United States Patent and Trademark Office*